US00PP29673P3

(12) United States Plant Patent
Katsumoto

(10) Patent No.: US PP29,673 P3
(45) Date of Patent: Sep. 18, 2018

(54) ***ROSA* PLANT NAMED 'FLORI 6101'**

(50) Latin Name: *Rosa hybrida*
Varietal Denomination: FLORI 6101

(71) Applicant: Yukihisa Katsumoto, Osaka (JP)

(72) Inventor: Yukihisa Katsumoto, Osaka (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 15/330,694

(22) Filed: Oct. 27, 2016

(65) Prior Publication Data

US 2018/0124966 P1 May 3, 2018

(51) Int. Cl.
*A01H 5/02* (2018.01)

(52) U.S. Cl.
USPC ..... Plt./130
CPC ..... *A01H 5/0222* (2013.01)

(58) Field of Classification Search
USPC ..... Plt./101, 130
See application file for complete search history.

*Primary Examiner* — Susan McCormick Ewoldt
(74) *Attorney, Agent, or Firm* — C. A. Whealy

(57) ABSTRACT

A new and distinct cultivar of Rose plant named 'FLORI 6101', characterized by its upright and strong flowering stems; moderately vigorous growth habit; dark green-colored leaves; double-type light violet-colored flowers; and excellent postproduction longevity.

1 Drawing Sheet

Botanical designation: *Rosa hybrida.*
Cultivar denomination: 'FLORI 6101'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'FLORI 6101'.

The new Rose plant is a naturally-occurring whole plant mutation of an unnamed proprietary *Rosa hybrida* selection, not patented. The new Rose plant was discovered and selected by the Inventor as a single flowering plant from within a population of plants of the mutation parent selection in a controlled greenhouse environment in Mishima, Osaka, Japan in August, 2010.

Asexual reproduction of the new Rose plant by vegetative cuttings in Mishima, Osaka, Japan since August, 2013 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'FLORI 6101'. These characteristics in combination distinguish 'FLORI 6101' as a new and distinct Rose plant:

1. Upright and strong flowering stems.
2. Moderately vigorous growth habit.
3. Dark green-colored leaves.
4. Double-type light violet-colored flowers.
5. Excellent postproduction longevity.

Plants of the new Rose differ from plants of the mutation parent primarily in flower color as mutation parent selection have very light purple-colored flowers.

Plants of the new Rose can be compared to plants of *Rosa hybrida* 'Ocean Song', not patented. In side-by-side comparisons, plants of the new Rose differ from plants of 'Ocean Song' in the following characteristics:

1. Flowers of plants of the new Rose are more rounded than and not as star-shaped as flowers of plants of 'Ocean Song'.
2. Flowers of plants of the new Rose are light violet in color whereas flowers of plants of 'Ocean Song' are very light purple in color.
3. Flowers of plants of the new Rose have fewer pistils than flowers of plants of 'Ocean Song'.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the top of the sheet is a side perspective of typical flowering plants of 'FLORI 6101' grown in a ground bed.

The photograph at the bottom of the sheet is a close-up view of a typical developed flower of 'FLORI 6101'.

DETAILED BOTANICAL DESCRIPTION

The aforementioned photographs, following observations and measurements describe plants grown in ground beds in a polyethylene-covered greenhouse in Bogota, Colombia and under typical cut Rose production practices. Plants were three months old when the photographs and description were taken. During the production of the plants, day temperatures averaged 25° C. and night temperatures averaged 10° C. In the following description, color references are made to The Royal Horticultural Society Colour Chart, 2001 Edition, except where general terms of ordinary dictionary significance are used.

Botanical classification: *Rosa hybrida* 'FLORI 6101'.

Parentage: Naturally-occurring whole plant mutation of an unnamed proprietary *Rosa hybrida* selection, not patented.

Propagation:

*Type*.—By vegetative cuttings.

*Time to initiate roots, summer*.—About three weeks at temperatures about 15° C. to 20° C.

*Time to initiate roots, winter*.—About four weeks at temperatures about 15° C. to 20° C.

*Time to produce a rooted young plant, summer*.—About six weeks at temperatures about 15° C. to 20° C.

*Time to produce a rooted young plant, summer*.—About eight weeks at temperatures about 15° C. to 20° C.

*Root description*.—Medium in thickness, fibrous; whitish in color.

*Rooting habit*.—Freely branching.

Plant description:

*Plant and growth habit*.—Perennial shrub; upright and strong flowering stems; typically grown as a standard-type cut flower; moderately vigorous growth habit.

*Plant height*.—About 131 cm.

*Lateral branches*.—Branching habit: Freely branching habit with numerous branches developing per plant. Texture: Smooth, glabrous; older stems, woody. Strength: Strong. Color: Close to 144C, becoming closer to 197B with development. Thorns: Density: Random, about nine per 15 cm of stem length. Shape: Triangular with sharp acuminate apices; slightly incurved. Height: About 9.8 mm. Color: Close to 84C.

Leaf description:

*Arrangement*.—Alternate; compound with typically five leaflets per leaf.

*Leaf length*.—About 13.2 cm.

*Leaf width*.—About 10 cm.

*Terminal leaflet length*.—About 6.2 cm.

*Terminal leaflet width*.—About 4.5 cm.

*Leaflet shape*.—Ovate.

*Leaflet apex*.—Acuminate.

*Leaflet base*.—Short attenuate.

*Leaflet margin*.—Doubly serrate.

*Leaflet texture and luster, upper and lower surfaces*.—Rough, pubescent; slightly glossy.

*Leaflet venation pattern*.—Pinnate, reticulate.

*Leaflet color*.—Developing and fully opened leaflets, upper surface: Close to 136A. Developing and fully opened leaflets, lower surface: Close to 138B.

*Petioles*.—Texture, upper and lower surfaces: Prickly. Color, upper and lower surfaces: Close to 146C tinged with close to 79B.

*Stipules*.—Arrangement and appearance: Two, adnate to the petiole, leafy in appearance. Length: About 2.5 cm. Shape: Roughly deltoid. Apex: Acuminate, tapered. Base: Tapered. Margin: Entire. Color, upper surface: Close to 148A. Color, lower surface: Close to 146B.

Flower description:

*Flower type and arrangement*.—Symmetrical double rosette flowers; flowers typically grown as standard-types; flowers face upright.

*Flowering season*.—Plants of the new Rose flower year-round under greenhouse conditions; early flowering habit, plants begin flowering about eight weeks after planting.

*Flower diameter*.—About 6.3 cm.

*Flower depth (height)*.—About 5.2 cm.

*Flower longevity*.—Excellent postproduction longevity; flowers maintain good substance for about 16 days as a cut flower; flowers persistent.

*Fragrance*.—None detected.

*Flower buds*.—Length: About 2.9 cm. Shape, cross-section: Broadly ovate. Color: Close to 144D.

*Petals and petaloids*.—Quantity: About 23 per flower; petals imbricate. Length: About 4.5 cm. Width: About 5.3 cm. Shape: Nearly round. Apex: Rounded acute. Base: Obtuse. Margin: Entire. Texture, upper and lower surfaces: Smooth, glabrous; somewhat leathery. Color: When opening and fully opened, upper surface: Close to 84C; color does not fade with development. When opening and fully opened, lower surface: Close to 84C; color does not fade with development.

*Sepals*.—Quantity per flower: Typically five forming a star-shaped calyx. Length: About 4.3 cm. Width: About 9.4 mm. Shape: Subulate. Apex: Acuminate. Base: Fused. Margin: Serrate. Texture, upper and lower surfaces: Somewhat leathery. Color: When opening and fully opened, upper surface: Close to 142C. When opening and fully opened, lower surface: Close to N144D.

*Peduncles*.—Length: About 4.7 cm. Diameter: About 4.8 mm. Strength: Strong. Angle: Upright. Texture: Smooth, glabrous. Color: Close to 144B tinged with close to N79D.

*Reproductive organs*.—Stamens: Quantity: About 123 per flower. Filament length: About 5.7 mm. Filament color: Close to 11D. Anther length: About 4.3 mm. Anther shape: Oblong. Anther color: Close to 19C. Pollen amount: None observed. Pistils: Quantity: About 88 per flower. Pistil length: About 9 mm. Pistil color: Close to 11D. Receptacle height: About 9.8 mm. Receptacle diameter: About 7.3 mm. Receptacle texture: Smooth, glabrous. Receptacle color: Close to 142B. Fruits and seeds: Fruit and seed development have not been observed on plants of the new Rose to date.

Pathogen & pest resistance: Plants of the new Rose have not been observed to be resistant to pathogens and pests common to Rose plants.

Temperature tolerance: Plants of the new Rose have been observed to tolerate temperatures ranging from about 5° C. to about 45° C.

It is claimed:

1. A new and distinct Rose plant named 'FLORI 6101' as illustrated and described.

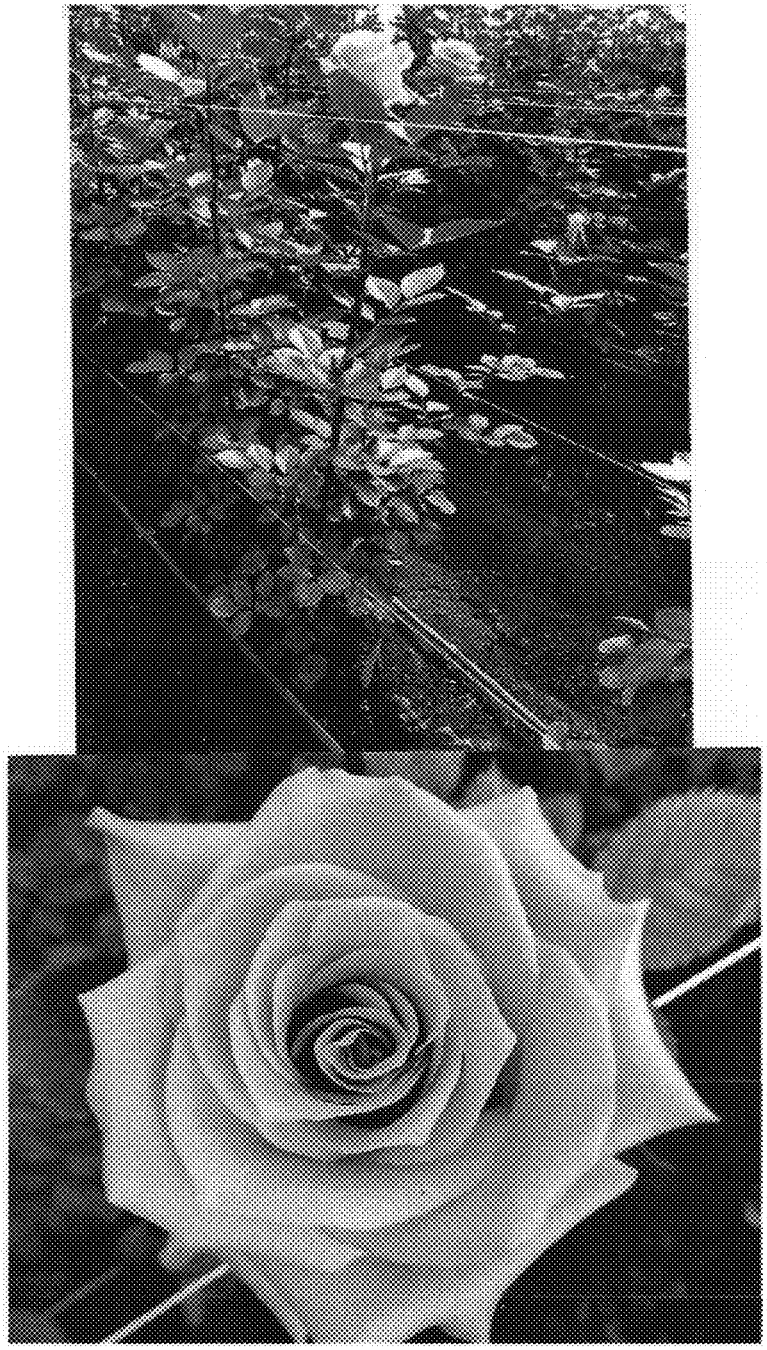

* * * * *